United States Patent [19]

Waugh

[11] Patent Number: 6,028,107
[45] Date of Patent: **\*Feb. 22, 2000**

[54] ORTHOMOLECULAR MEDICAL USE OF L-CITRULLINE FOR VASOPROTECTION, RELAXATIVE SMOOTH MUSCLE TONE AND CELL PROTECTION

[76] Inventor: William Howard Waugh, 119 Oxford Rd., Greenville, N.C. 27858

[*] Notice: This patent is subject to a terminal disclaimer.

[21] Appl. No.: 08/807,757

[22] Filed: Feb. 27, 1997

[51] Int. Cl.[7] .................................................. A61K 31/195
[52] U.S. Cl. ........................... 514/563; 514/561; 514/563
[58] Field of Search ....................................... 514/563, 561

[56] References Cited

PUBLICATIONS

Nicolodi et al. (AN 1998067064, Medline, abstract of Int. J. of Clinical Pharmacolgy Research, (1997), 17 (2–3), 85–8), 1997.

Nicolodi et al. (AN 1998067064, Medline, abstract of Int. J. of Clinical Pharmacolgy Research, (1997), 17 (203), 85–8), 1997.

Mandell et al. (AN 970008969, Medline, abstract of Parental Diagonosis, (1996 May), 16 (5), 419–424, 1996.

Armstrong, M.D. et al, "A Study of Plasma Free Amino Acid Levels. II. Normal Values for Children and Adults", Metab. 22:561–569 (1973).

Arnal, J.–F. et al, "Interactions between L–Arginine and L–Glutamine Change Endothelial No Production", J. Clin. Invest. 95:2565–2572 (1995).

Banay–Schwartz, M. et al, "Changes with Aging in the Levels of Amino Acids in Rat CNS Structural Elements: IV. Methionine and Basic Amino Acids", J. Neurosc. Res. 26:217–223 (1990).

Barbul, A., "Arginine: Biochemistry, Physiology, and Therapeutic Implications", J. Parenteral Enteral Nutr. 10:227–238 (1986).

Becker, R.C., "Antiplatelet Therapy", Sci. Med. 3:12–21 (1996).

Bogle, R.G. et al, "Bradykinin and ATP Stimulate L–Arginine Uptake and Nitric Oxide Release in Vascular Endothelial Cells", Biochem. Biophys. Res. Commun. 180:926–932 (1991).

Boysen, G. et al, "Prolongation of Bleeding Time and Inhibition of Platelet Aggregation by Low–Dose Acetylsalicylic Acid in Patients with Cerebrovascular Disease", Stroke 15:241–243 (1984).

Bucala, R. et al, "Advanced Glycosylation Products Quench Nitric Oxide and Mediate Defective Endothelium–dependent Vasodilation in Experimental Diabetes", J. Clin. Invest. 87:432–438 (1991).

Buchmann, I. et al, "Effect of Arginine Administration on Plasma and Brain Levels of Arginine and Various Related Amino Compounds in the Rat", Pharmacol. 53:133–142 (1996).

Buniatan, H.C. et al, "Urea Synthesis by Brain", J. Neurochem. 13:743–753 (1966).

(List continued on next page.)

*Primary Examiner*—Jose' G. Dees
*Assistant Examiner*—Sabiha N. Qazi

[57] ABSTRACT

This invention is a novel method in orthomolecular medicine to sustain favorable amounts of L-arginine efficiently within the human body for preservation of good health and amelioration of various disease states. The method provides administration of sizable amounts of L-citrulline as precursor substance for bioconversion to L-arginine in order to maintain greater blood plasma concentrations of L-arginine as potential substrate for various metabolic functions. The method is useful to increase the availability of substrate for nitric oxide production by constitutive nitric oxide synthases. Embodiments include uses of exogenous L-citrulline for more vasoprotection in sickle cell disease and atherosclerosis, more stability in circulating platelets, more relaxative smooth muscle tone during pregnancy and in achalasia, greater defense against restenosis after angioplasty, greater defense against oxidative stress, enhanced cell stores of creatine, and enhanced fertility in males with oligospermia.

19 Claims, 1 Drawing Sheet

OTHER PUBLICATIONS

Calloway, D.H., "Nutrition and Reproduction Function of Men", Nutr. Absts. Revs. 53:361–382 (1983).

Caplan, L.R., "Intracranial Branch Atheromatous Disease", Neurol 39:1246–1250 (1989).

Carter, A.J. et al, "Preincubation with Creatine Enhances Levels of Creatine Phosphate and Prevents Anoxic Damage in Rat Hippocampal Slices", J. Neurochem. 64:2691–2699 (1995).

Castillo, L. et al, "Plasma Arginine and Citrulline Kinetics in Adults Given Adequate and Arginine–free Diets", Proc. Natl. Acad. Sci. USA 90:7749–7753 (1993).

Chaudhuri, G. et al, "No is More Important Than PG12 in Maintaining Low Vascular Tone in Feto–Placental Vessels" Am. J. Physiol. 265:2036H–2043H (1993).

Chen, F.–Y. et al, "Arginine Synthesis from Citrulline in Perivascular Nerves of Cerebral Artery", J. Pharmacol. Exptl. Therap. 273:895–901 (1995).

Compo, C. et al, "Aging Abolishes the Renal Response to L–Arginine Infusion in Essential Hypertension", Kidney Intern. 49 (Suppl. 55):S–126–S–128 (1996).

Cooke, J.P. et al, "Antiatherogenic Effects of L–Arginine in the Hypercholesterolemic Rabbit", J.Clin. Invest. 90:1168–1172 (1992).

Cooke, J.P. et al, "Cellular Mechanisms of Atherogenesis and the Effects of Nitric Oxide", Current Opinion Cardiol. 7:799–804 (1992).

Creager, M.A. et al, "L–Arginine Improves Endothelium–Dependent Vasodilation in Hypercholesterolemic Humans", J. Clin. Invest. 90:1248–1253 (1992).

Current Medical Diagnosis and Treatment, 1997, ed. by T.M. Tierney Jr. et al in: 36th ed., Appleton & Lange (1997), pp. 553–554.

De Belleroche, J. et al, in: The Headaches, ed. by J. Olesen et al, Raven Press, (1993), pp. 185–191.

Dhanakoti, S.N. et al, "Renal Arginine Synthesis:Studies in vitro and vivo", Am. J. Physiol. 259:E437–E442 (1990).

Diederich, D. et al, "Endothelial Dysfunction in Mesenteric Resistance Arteries of Diabetic Rats: Role of Free Radicals", Am. J. Physiol. 266:H1153–H1161 (1994).

Dörner, K. et al, "Referenzwerte für Plasmaaminosäuren im Verlauf der Schwangerschaft", Z. Geburtsh. u. Perinat. 197:141–143 (1993).

Drexler, H. et al, "Correction of Endothelial Dysfunction in Coronary Microcirculation of Hypercholesterolaemic Patients by L–Arginine", Lancet 338:1546–1550 (1991).

Duits, A.J. et al, "Enhanced Levels of Soluble VCAM–1 in Sickle Cell Patients and Their Specific Increment During Vasoocclusive Crisis", Clin. Immunol. Immunopathol. 81:96–98 (1996).

Egashira, K. et al, "Evidence of Impaired Endothelium–dependent Coronary Vasodilation in Patients with Angina Pectoris and Normal Coronary Angiograms", New Eng. J. Med. 328:1659–1664 (1993).

Fabricius, M. et al, "Arginine–Nitric Oxide Pathway and Cerebrovascular Regulation in Cortical Spreading Depression", Am. J. Physiol. 269:H23–H29 (1995).

Fitch, W.L. et al, "Plasma Amino Acid, Glucose, and Insulin Responses to Moderate–Protein and High–Protein Test Meals in Pregnant, Nonpregnant, and Gestational Diabetic Women", Am. J. Clin. Nutr. 46:243–249 (1987).

Förstermann, U. et al, "Nitric Oxide Synthase Isozymes", Hypertension 23:1121–1131 (1994).

Francis, R.B. Jr. et al, "Vascular Occlusion in Sickle Cell Disease: Current Concepts and Unanswered Questions", Blood 77:1405–1414 (1991).

Guichard, P. et al, "Diabetic Cardiomyopathy: The Significance of Creatine", Medical Hypotheses 45:41–44 (1995).

Halliwell, B., "Antioxidants in Human Health and Disease", Annu. Rev. Nutr. 16:33–50 (1996).

Hamon, M. et al, "Long–term Oral Administration of L–Arginine Reduces Intimal Thickening and Enhances Neoendothelium–dependent Acetylcholine–induced Relaxation after Arterial Injury", Circulation 90:1357–1362 (1994).

Harker, L.A. et al, "The Role of Platelets in Acute Vascular Events", Circulation 62:Suppl. V, V–13–V–18 (1980).

Harman, D., "Free Radical Involvement in Aging", Drugs & Aging 3:60–80 (1993).

Harris, R.C. et al, "Elevation of Creatine in Resting and Exercised Muscle of Normal Subjects by Creatine Supplementation", Clinical Sci. 83:367–374 (1992).

Heinzel, B. et al, "Ca2+/Calmodulin–dependent Formation of Hydrogen Peroxide by Brain Nitric Oxide Synthase", Biochem. J. 281:627–630 (1992).

Jones, M.E., "Conversion of Glutamate to Ornithine and Proline: Pyrroline–5–Carboxylate, a Possible Modulator of Arginine Requirements", J. Nutr. 115:509–515 (1985).

Kamoun, P. et al, "Citrulline Concentrations in Human Plasma after Arginine Load", Clin. Chem. 37:1287 (1991).

Kanner, J. et al, "Nitric Oxide as an Antioxidant", Archiv. Biochem. Biophys. 289:130–136 (1991).

Kanner, J. et al, "Nitric Oxide, an Inhibitor of Lipid Oxidation by Lipoxygenase, Cyclooxygenase and Hemoglobin", Lipids 27:46–49 (1992).

Kantor, D.B. et al, "A Role for Endothelial No Synthase in LTP Revealed by Adenovirus–Mediated Inhibition and Rescue", Science 274:1744–1748 (1996).

Keller, D.W. et al, "L–Arginine Stimulation of Human Sperm Motility in vitro", Biol. Reproduct. 13:154–157 (1975).

Kerle, K.K. et al, "Exertional Collapse and Sudden Death Associated with Sickle Cell Trait", Mil. Med. 161:766–767 (1996).

Lambert, G.A. et al, "Cortical Spreading Depression Reduces Dura Blood Flow—A Possible Mechanism for Migrain Pain?", Cephalalgia 14:430–436 (1994).

Lauritzen, M., "Pathophysiology of the Migraine Aura—The Spreading Depression Theory", Brain 117:199–210 (1994).

Lauritzen, M., "Pathophysiology of the Migraine Aura", Sci. Med. 3:32–41 (1996).

Liesner, R.J. et al, "Sudden Death in Sickle Cell Disease", J. Royal Soc. Med. 86:484–485 (1993).

Lloyd–Jones, D.M. et al, "The Vascular Biology of Nitric Oxide and Its Role in Atherogenesis", Annu. Rev. Med. 47:365–375 (1996).

MacDonald, P.C. et al, "Preterm Birth", Scient. Am. Sci. Med. 3:42–51 (1996).

Mannick, J.B. et al, "Nitric Oxide Produced by Human B Lymphocytes Inhibits Apoptosis and Epstein–Barr Virus Reactivation" Cell 79:1137–1146 (1994).

Martindale The Extra Pharmacopoeia, 30 th. edition, ed. by J.E.F. Reynolds, Pharmaceutical Press, (1993) pp. 1038, 1517, 1582, 1649, 1770, 1839, 1914, 2037.

Mayer, B. et al, "Biosynthesis of Endothelium–Derived Relaxing Factor: A Cytosolic Enzyme in Porcine Aortic Endothelial Cells $Ca^{2+}$—Dependently Converts L–Arginine into and Activator of Soluble Guanyl Cyclase", Biochem. Biophys. Res. Commun. 164:678–685 (1989).

McClain, P.E. et al, "Relationship of Maternal Amino Acid Profiles at 25 Weeks of Gestation to Fetal Growth", Am. J. Clin. Nutr. 31:401–407 (1978).

Michaelis, T. et al, "Absolute Concentration of Metabolites in the Adult Human Brain in Vivo: Quantification of Localized Proton MR Spectra", Radiology 187:219–227 (1993).

Molnar, M. et al, "Prolonged Blockade of Nitric Oxide Synthesis in Gravid Rats Produces Sustained Hypertension, Proteinuria, Thrombocytopenia, and Intrauterine Growth Retardation", Am. J. Obst. Gynecol. 170:1458–1466 (1994).

Moncada, S. et al, "The L–Arginine–Nitric Oxide Pathway", New Engl. J. Med. 329:2002–2012 (1993).

Moriguti, J.C. et al, "Fasting Plasma Free Amino Acid of Elderly Men", Amino Acids 9:46 (1995).

Morikawa, E. et al, "L–Arginine Decreases Infarct Size Caused by Middle Cerebral Arterial Occlusion in SHR", Am. J. Physiol. 263:H1632–H1635 (1992).

Muruganandam, A. et al, "Isolation of Nitric Oxide Synthase from Human Platelets", Biochim. Biophys. Acta 1200:1–6 (1994).

Noeh, F.M. et al, "The Effects of Arginine Administration on the Levels of Arginine, Other Amino Acids and Related Amino Compounds in the Plasma, Aorta, Vena Cava, Bronchi and Pancreas of the Rat", Life Sciences 58:PL 131–138 (1996).

Palmar, T. et al, "The Effect of Protein Loads on Plasma Amino Aicd Levels", Clin. Sc. Molec. Med. 45:827–832 (1973).

Pauling, L., "Orthomolecular Somatic and Psychiatric Medicine", Vitalstoffe Zivilisations Krankheiten, 13:3–5 (1968).

Perry, T.L. et al, "CSF Amino Acids and Plasma—CSF Amino Acid Rations in Adults", J. Neurochem. 24:587–589 (1975).

Pow, D.V., "Immunocytochemical Evidence for a Glial Localisation of Arginine and a Neuronal Localisation of Citrulline in the Rat Neurohypophysis: Implications for Nitrergic Transmission", Neurosci. Lett. 181:141–144 (1994).

Radomski, M.W. et al, "An L–Arginine/Nitric Oxide Pathway Present in Human Platelets Regulates Aggregation", Proc. Natl. Acad. Sci. USA 48:5193–5197 (1990).

Reid, M.E., "Reactive Oxygen and Nitric Oxide in Skeletal Muscle", News Physiol. Sci. 11:114–119 (1996).

Reyes, A. A., "L–Arginine Administration Prevents Glomerular Hyperfiltration and Decreases Proteinuria in Diabetic Rats", J. Am. Soc. Nephrol. 4:1039–1045 (1993).

Roberts, J.M. et al, "Preclampsia: an Endothelial Cell Disorder", Am. J. Obstet. Gynecol. 161:1200–1204 (1989).

Ross, R. et al, "Hyperlipidemia and Atherosclerosis", Science 193:1094–1100 (1976).

Rothnagel, J.A. et al, "Citrulline in Proteins from the Enzymatic Determination of Arginine Residues", in: Methods in Enzymology, 107(B), Academic Press (1984), pp. 624–631.

Sadasivudu, B. et al, "Studies on Functional and Metabolic Role of Urea Cycle Intermediates in Brain", J. Neurochem. 27:785–794 (1976).

Schachter, A. et al, "Treatment of Oligospermia with the Amino Acid Arginine", J. Urol. 110:311–313 (1973).

Schmidt, H.H.H.W. et al, "No at Work", Cell 78:919–925 (1994).

Schoengold, D.M. et al, "Free Amino Acids in Plasma Throughout Pregnancy", Am. J. Obstet. Gynecol. 131:490–499 (1978).

Scriver, C.R. et al, "Normal Plasma Free Amino Acid Values in Adults: The Influence of Some Common Physiological Variables", Metabl. 34:868–873 (1985).

Silberstein, S.D. et al, in: Wolff's Headache and Other Head Pain, 6th ed., ed. by Dalessio, D.L. et al, Oxford Univ. Press (1993), p. 115.

Simonian, N.A. et al, "Oxidative Stress in Neurodegenerative Diseases", Annu. Rev. Pharmacol. Toxicol. 36:83–106 (1996).

Smoyer, W.E. et al, "Enhanced GFR Response to Oral Versus Intravenous Arginine Administration in Normal Adults", J. Lab. Clin. Med. 118:166–175 (1991).

Stadtman, E.R., "Minireview: Protein Modification in Aging", J. Gerontol. 43:B112–B120 (1988).

Stamler, J.S., "Redox Signaling: Nitrosylation and Related Target Interations of Nitric Oxide", Cell 78:931–936 (1994).

Steinberg, M.H., "Review: Sickle Cell Disease: Present and Future Treatment", Am. J. Med. Sci. 312:166–174 (1996).

Tsao, P.S. et al, "Enhanced Endothelial Adhesiveness in Hypercholesterolemia is Attenuated by L–Arginine", Circulation 89:2176–2182 (1994).

Vasta, V. et al, "Identification of a Specific Transport System for L–Arginine in Human Platelets", Biochem. Biophys. Res. Commun. 206:878–884 (1995).

Visek, W.J., "Arginine and Disease States," J. Nutr., 115:532–541 (1985).

Walker, J.B., "Creatine: Biosynthesis, Regulation, and Function", Adv. Enzymol. 50:178–242 (1979).

Windmueller, H.G. et al, "Source and Fate of Circulating Citrulline", Am. J. Physiol. 241:E473–E480 (1981).

Wolters, H.J. et al, "Low–intensity Oral Anticoagulation in Sickle–Cell Disease Reverses the Prethrombotic State: Promises for Treatment?", Brit. J. Haematol. 90:715–717 (1995).

Wu, K.K. et al, "Role of Endothelium in Thrombosis and Hemostasis", Annu. Rev. Med. 47:315–331 (1996).

Wurtman, R.J., "Nutrients that Modify Brain Function", Sci. Am. 246:50–59 (1982).

Xia, Y. et al, "Nitric Oxide Synthase Generates Superoxide and Nitric Oxide in Arginine–depleted Cells Leading to Peroxynitrite–mediated Cellular Injury", Proc. Natl. Acad. Sci. USA, 93:6770–6774 (1996).

Yallampalli, C. et al, "Nitric Oxide Inhibits Uterine Contractility During Pregnancy but Not During Delivery"Endocrinol. 133:1899–1902 (1993).

Yearick, E.S. et al, "Serum Amino Aicd Response to Isocaloric Test Meals", Am. J. Clin. Nutr. 20:338–344 (1967).

Young, V.R. et al, pp. 191–232 (Chapter 13) in: Amino Acid Metabolism and Therapy in Health and Nutritional Disease, ed. by L.A. Cynober, CRC Press (1995).

Zeiher, A.M. et al, "Endothelium–Mediated Coronary Blood Flow Modulation in Humans", J. Clin. Invest. 92:652–662 (1993).

ORTHOMOLECULAR MEDICAL USE OF L-CITRULLINE FOR VASOPROTECTION, RELAXATIVE SMOOTH MUSCLE TONE AND CELL PROTECTION

SUMMARY OF THE INVENTION

A novel method is provided to increase efficiently the net rate of synthesis of available L-arginine in humans. It entails peroral supplementation with L-citrulline in substantial amounts for better health and amelioration of diseases that are not urea-cycle enzyme/substrate liver disorders. The method is an example of orthomolecular medicine in that it uses a substance normally present in the human body to increase uniquely the availability of another substance that is also present normally in the human body, for better health and the treatment of disease. These two substances are the amino acids, L-citrulline and L-arginine, respectively.

The method entails alimentary tract absorption of L-citrulline that is ingested daily in sizable amounts supplementary to the usually very small amounts of L-citrulline in food intakes. The absorbed L-citrulline in portal venous blood bypasses appreciable uptake by the liver and it is distributed in blood largely to kidneys, brain, and other tissues for bioconversions to L-arginine for local physiologic purposes and for distribution of the formed L-arginine to other sites for physiologic functions.

These functions include L-arginine use for biosynthesis of cell proteins and cell creatine and for supply of more available L-arginine as rate-limiting substrate for nitric oxide production by activated constitutive nitric oxide synthases. Constitutive nitric oxide synthases are located in endothelial cells, platelets, smooth muscle cells, gliacytes and neurocytes of the nervous system, and other cells of the body. By increasing the concentrations of L-arginine in extracellular fluids for cell entry and greater L-arginine levels intracellularly, the constitutive production of nitric oxide is expected to be increased catalytically by constitutive isozymes from L-arginine in the local microenvironments. Cell levels of creatine are also embodied to increase because of more available L-arginine as precursor. Expected are greater relaxative smooth muscle tone in blood vessels, in uteri and fetoplacental blood vessels during pregnancies, and in the esophagus in achalasia; also greater stability in circulating platelets and greater vasoprotection against abnormal proliferative changes and atherogenesis; better nutritional support during pregnancy; enhanced male fertility; enhanced creatine stores in myocytes and neurocytes, and greater nitric oxide present locally as scavenger of reactive oxygen species during oxidative stress in ischemic injury, diabetes mellitus, and aging.

Beneficial therapeutic effects are expected in acute and chronic events in sickle cell disease, migraine pains, ischemic strokes, lacunar infarctions, coronary and peripheral atherosclerotic and vasospastic diseases, preeclampsia, prevention of restenosis after angioplasty, spontaneous pre-term labor for tocolysis and lessening of fatigue during muscular and neural activities. For the above indications, it is contemplated that L-citrulline can be used in humans in acute dosage range from about 2.5 to about 25 grams per day and in chronic dosage range from about 1.8 to about 15 grams per day.

BRIEF DESCRIPTION OF THE DRAWING SHEET

The one FIGURE contains graphs of plasma ultrafiltrate levels of L-arginine in the fasting state (9–10 hours) related to the daily amounts of L-citrulline ingested in two divided doses in a male of 102 kg. Also depicted are levels 2-hours after ingestion of morning doses of L-citrulline (EXAMPLE 1).

TECHNICAL FIELD

This invention relates to the field of orthomolecular medicine for the preservation of good health and the amelioration of disease by a novel means of nutritional supplementation.

BACKGROUND OF THE INVENTION

Orthomolecular medicine is the term coined by Linus Pauling for the preservation of good health and the treatment of disease by varying the concentrations in the body of substances that are normally present in the body and are required for optimal or better health. Pauling, L., Vitalstoffe Zivilisations Krankheiten 13:3–5, (1968). L-arginine is viewed a nonessential amino acid in humans for nitrogen balance and for metabolic purposes in that L-arginine can be synthesized in the human body in sufficient amounts without dietary supply of this amino acid except for optimum growth in young children and for select metabolic disorders involving hepatic ureagenesis and for stress states. Visek, W. J., J. Nutri. 115:531–541, (1985); Barbul, A., J. Parenteral Enteral Nutr. 10:227–238, (1986); Young, V. R. et al, pp. 191–243, in: Amino Acid Metabolism and Therapy in Health and Nutritional Disease, CRC Press, (1995).

L-citrulline is also viewed a nonessential amino acid in humans for nitrogen balance and metabolic purposes without supplemental supply of L-citrulline. This amino acid is not a component of most proteins within the human body except for some specialized proteins in cells in the epidermis, hair, and in myelin. Rothnagel, J. A. et al, pp. 624–631, in: Methods in Enzymology, Academic Press, (1984).

L-arginine is a normal constituent of numerous body proteins and is associated with a variety of essential metabolic cell reactions including the initial amidinotransferase (E.C.26.21) reaction with glycine for creatine synthesis. Barbul, A., (1986); Young, V. R. et al, (1995). L-arginine also is a unique endogenous substrate for constitutive nitric oxide synthase (c-NOS) for production of the effector free radical, nitric oxide, in the L-arginine-nitric oxide pathway for messenger agent. Schmidt, H. H. H. W. et al, Cell 78:919–925, (1994).

L-glutamine is another dietary nonessential amino acid that is in body fluids and it is derived from skeletal muscle metabolism of amino acids as a major endogenous source of l-glutamine as precursor for the intestinal synthesis of L-citrulline. Young, V. R. et al, (1995). Without appreciable liver uptake of intestinal-derived L-citrulline in portal venous blood, L-citrulline is distributed by circulating blood to the kidneys, brain, and other cells. Windmueller, H. G. et al, Am. J. Physiol. 241:E473–E480, (1981). In these tissues, there is de novo cell conversion of L-citrulline to L-arginine for cell protein synthesis and other purposes. Jones, M. E., J. Nutr. 115:509–515, (1985).

Plasma L-citrulline availability to the kidneys appears to be the major important factor in determining the rate of endogenous (extrahepatic) arginine synthesis, based largely in nonhuman models. Dhanakoti, S. N. et al, Am. J. Physiol. 259:E437–E442, (1990). However, it has been assumed, but not known with confidence that this scheme applies equally to human subjects. Young, V. R. et al, (1995).

On the other hand, circulating blood plasma and whole body L-arginine homeostasis in healthy human subjects is believed to be achieved principally by modulation in the level of dietary arginine intake and/or by regulation in the rate of L-arginine degradation. This concept is based partly on the evidence that the rate of conversion of plasma citrulline to plasma arginine was found to be similar during the fast and fed states in healthy human subjects adapted to an arginine-rich (adequate) or arginine-free diet. Castillo, L. et al, Proc. Natl. Acad. Sci. USA, 90:7749–7753, (1993); Young V. R. et al, (1995). A change in arginine synthesis in extrahepatic tissues is said not to be an important component to arginine homeostasis in the face of altered physiologic or pathologic states. The net rate of de novo arginine synthesis in human subjects is believed not to be profoundly affected by acute changes in the dietary intake level of arginine. Instead, arginine homeostasis is considered more likely to be achieved by changing rates of L-arginine degradation in relation to the prevailing metabolic conditions of the host subject and the dietary intake level of L-arginine. Young, V. R. et al, (1995).

Supplemental oral 3-gram single doses in healthy humans raises plasma arginine levels acutely, but without a change in plasma citrulline levels. Kamoun, P. et al, Clin. Chem. 37:1287, (1991). Based on studies in rats, after parenteral injection, of extra arginine, the concentrations of arginine in plasma and various tissues return to normal in about 2 to 3 hours as the plasma half-life is very short at about 1 hour. These pharmacokinetics of administered arginine is used to cast doubt on the usefulness of arginine sold in many health food stores, where consumers buy arginine preparations because of a variety of reputed, yet unproven, health benefits. Noeh, F. M. et al, Life Sciences 58:131–138(1996).

In humans, the rate of uptake or utilization by liver and other tissues of arginine is so rapid after ingestion of a single protein meal of about 30 to 50 grams of proteins (containing about 1 to 2 grams of arginine) that peripheral plasma arginine levels peak within 2 to 3 hours and return to near fasting levels in about 5 to 6 hours. Yearick, E. S. et al, Am. J. Clin. Nutr. 20:338–344 (1967); Palmer, T. et al, Clin. Sc. Molec. Med. 45:827–832 (1973).

In normal adults, plasma levels of arginine peak at about 1 hour to about 3.6-times greater than fasting values of 90±6 $\mu$M (mean±SEM) after ingestion of 24.8 grams of L-arginine (as 30 grams of arginine hydrochloride), but plasma levels return to near fasting values in 3 hours. Smoyer, W. E. et al, J. Lab. Clin. Med. 118:166–175, (1991). A single oral dose of 24.8 grams of free arginine may be estimated to be about 4.7-times greater than the total amount of arginine that is ingested daily in humans consuming a moderately high protein diet of 1.5 grams/kg body weight for a 70 kg person (with assumption that the arginine content in the protein is about 5%), about 5.25 grams of arginine!

Overnight fasting levels of arginine in blood plasma of healthy American children aged 6 to 18 are reported to be 89±20 $\mu$M (mean±SD) and the overnight fasting levels of healthy adult men and women are reported as 89±26 and 75±24 $\mu$M, respectively. Armstrong, M. D. et al, Metab. 22:561–569, (1973). Similar overnight fasting values for plasma arginine concentrations of healthy adults are reported by other workers, e.g. 84±22 $\mu$M and 94±20 $\mu$M (mean±SD), respectively. Perry et al, J. Neurochem. 24:587–589, (1975); Scriver, C. R. Metab. 34:868–873, (1985). Overnight fasting plasma values of arginine are strikingly lower in healthy women during late normal pregnancy, viz. decline from 89±20.8 $\mu$M to 43.4±5.6 $\mu$M. Fitch, W. F. et al, Am. J. Clin. Nutr. 46:243–249, (1987). Similarly, fasting plasma arginine levels are significantly lower (65±14 $\mu$M) in elderly men of well-fed good health, possibly related to the aging process or due to lower protein intake. Mariguti, J. C. et al, Amino Acids 9:46, (1995).

Various isozymes of nitric oxide synthase (EC 1.14.13.39) have been identified as being responsible for the constitutively expressed synthesis (continuously present, though not always active enzyme) of nitric oxide as an initial important product. L-arginine is the nitrogenous substrate for the enzymatic product of nitric oxide by constitutive nitric oxide synthase (c-NOS) activity and L-citrulline is formed stociometrically as a coproduct. Constitutive isozymes are present in endothelial cells, in central and peripheral neuronal cells, in epithelial cells, and many other cells of the body, including human blood platelets. Forstermann, U. et al, Hypertension 23:1121–1131, (1994); Radomski, M. W. et al, Proc. Natl. Acad. Sci. USA 87:5193–5197, (1990); Murunganandam, A. et al, Biochim, Biophys. Acta 1200:1–6, (1994); Vasta, V. et al, Biochem. Biophys. Res. Commun. 206:878–884, (1995).

The synthesis of nitric oxide constitutively by vascular endothelium is responsible continuously for vasodilator tone, the control of platelet aggregation and adhesion, and the inhibition of leukocyte activation and adhesion. Thus, endothelium-derived nitric oxide via the L-arginine-nitric oxide pathway is vasoprotective. Moncada, S. et al. New Engl. J. Med. 329:2002–2012, (1993); Schmidt, H. H. H. W. et al. Cell 78:919–925, (1994). Endothelium-derived nitric oxide potentially antagonizes all stages of platelet activation.

Platelets themselves generate nitric oxide by the L-arginine-nitric oxide pathway mediated by constitutive NOS within platelets. This platelet pathway acts as a negative pathway to stabilize platelet function.

Utilization of L-arginine as substrate for platelet c-NOS serves as autocrine control of platelet function and the availability of extracellular L-arginine for a specific platelet transporter of this substrate is contributory to vasoprotection and antithrombotic effect. Radomski, M. W. et al, (1990); Muruganandam, A. et al; Vasta, V. et al, (1995).

The apparent Michaelis constant ($K_m$) of L-arginine for purified endothelial c-NOS in vitro is about 6 $\mu$M (the concentration of substrate when the velocity of enzymatic reaction is half-maximal). However, the concentration for maximal stimulation of the purified c-NOS is much higher, between 30 and 100 $\mu$M. Mayer, B. et al, Biochem. Biophys. Res. Commun. 164:678–685, (1989). In the presence of extracellular L-glutamine concentration at level within a common normal plasma value in humans (600 $\mu$M), endothelial production of nitric oxide generated by c-NOS in vitro is directly dependent upon the extracellular concentrations of L-arginine above 10 $\mu$M to levels of 1,000 $\mu$M and more without apparent saturation of the enzyme. Arnal, J. F. et al, J. Clin. Invest. 95:2565–2572, (1995). Thus, the functional apparent $K_m$ of extracellular L-arginine in vivo for constitutive endothelial generation of nitric oxide in intact cells is very much greater than that of the purified c-NOS near 6 $\mu$M.

This discrepancy termed "the arginine paradox" underlies apparently the fact that much in vivo data shows that increasing plasma L-arginine concentrations in circulating blood above normal fasting mean values of about 75 to 90 $\mu$M augments endothelial nitric oxide production by activated c-NOS. Föstermann, U. et al, (1994). Intracellular concentration of L-arginine does become rate-limiting for nitric oxide production in endothelial cells when stimulated under certain conditions and these cells can utilize exogenous L-arginine for nitric oxide catalytic formation. Bogle, R. G. et al, Biochem. Biophys. Res. Commun. 180:926–932, (1991).

With L-arginine infusion into humans with hypercholesterolemia, impaired endothelium-dependent vasodilation is corrected, which is mediated through nitric oxide generation. Drexler, H. et al, Lancet 338:1546–1550, (1991); Creager, M. A. et al, J. Clin. Invest. 90:1248–1253, (1992).

Vascular injury and hypercholesterolemia enhance adhesiveness of vascular endothelium to platelets and leukocytes and enhance vascular proliferation. These are viewed critical processes in atherogenesis. A twofold increase in plasma arginine levels induced by a sixfold enrichment of dietary L-arginine improves nitric oxide-dependent vasodilation associated with antiatherogenesis and markedly inhibits endothelial adhesiveness and atherogenesis in hypercholesterolemic rabbit models. In the rabbit model, alterations in nitric oxide activity are viewed as playing critical roles. Cooke, J. P. et al, J. Clin. Invest. 90:1168–1172, (1992); Tsao, P. S. et al, Circulation 89:2176–2182, (1994). Thus, generated endothelial nitric oxide, derived from L-arginine and oxygen by c-NOS, has potent antiplatelet and antiproliferative roles. Cooke, J. P. et al, Current Opinion Cardiol. 7:799–804, (1992). Neither L-arginine nor its amino acid precursor, L-citrulline, is currently suggested or used as dietary supplements for platelet antagonistic, antithrombotic, or vasoprotective effects. Becker, R. C. Sci. Med. 3:12–21, (1996).

The apparent $K_m$ of L-arginine for its uptake into human platelets is reported at 26±4 $\mu$M and 300 $\mu$M extracellular concentration of L-glutamine, L-lysine, or L-ornithine is inhibitory to L-arginine uptake at 30 $\mu$M concentration. Vasta et al, (1995). It is viewed that varying concentrations of L-arginine in plasma may change the uptake of this amino acid into human platelets and consequently its substrate availability for platelet nitric oxide synthesis and platelet stability. Vasta et al, (1995).

Endothelial-dependent vasodilation, mediated through nitric oxide generation, is impaired also with advanced aging and increasing hypercholesterolemia. Zieher, A. M. et al, J. Clin. Invest. 92:652–662, (1993). Advanced non-enzymatic glycolation end products, which accumulate in the vascular endothelium and subendothelium in aging and diabetes mellitus, have been shown to quench formed nitric oxide and mediate defective endothelium-dependent vasodilation. Bucala, R. et al, J. Clin. Invest. 89:432–438, (1991). Aging is viewed producing a derangement of endothelium function in essential hypertension since renal vasodilatory responses to L-arginine were blunted in aged compared to young hypertensives. Compo, C. et al, Kidney Int. 49 (Suppl. 55):S-126–S-128, (1996).

Endothelial secretion of nitric oxide, a diffusible agent, is thought to be released primarily into the abluminal side where it activates smooth muscle relaxative vasodilation and antiproliferative functions. This molecule also diffuses into the luminal side of blood vessels where this product formed by c-NOS with L-arginine is an important vasoprotective and antithrombotic mediator. Wu, K. K. et al, Annu. Rev. Med. 47:315–331, (1996).

After arterial injury in a rabbit model of angioplasty with endothelial denudation, long-term daily addition of L-arginine hydrochloride to 2.25% in the drinking water, which increased plasma arginine levels about 2.6-times, reduced thickening and enhanced neoendothelium-dependent arterial muscle relaxation. Hamon, M. et al, Circulation 90:1357–1362, (1994).

Clinically, platelets are postulated to have an important adverse role in many acute and chronic cardiovascular events including disorders of microvascular occlusions and vasospasms. Harker, L. A. et al, Circulation 62 (Suppl. V):V-13–V-18, (1980). Nitric oxide formation from endothelial c-NOS activity has critical roles in the maintenance of vascular homeostasis. However, therapeutic strategies for vascular augmentation of enzymatic nitric oxide production for beneficial prevention and/or the amelioration of atherosclerosis or other diseases or for the attenuation of neointimal formation after endothelial injury, including direct supplementation of NOS substrate (L-arginine) or co-factors (such as tetrahydrobiopterin), have not been developed for efficacious, practical use in humans. Lloyd-Jones, D. M. et al, Annu. Rev. Med. 47:367–375, (1996).

Oral strategies also have not yet been designed or reduced to practice in humans using L-citrulline as precursor for efficiently increasing the potential endogenous production of nitric oxide through increased activity of constitutive nitric oxide synthesas by increased availability of L-arginine for vasoprotection, neuroprotection, antithrombotic effects and myorelaxant effects via the L-arginine-nitric oxide pathway. Schmidt, H. H. H. W. et al, (1994). Also, similar oral strategies are not in the art for indirectly resulting in sustained luxus plasma concentrations of L-arginine for other healthy functions such as protein biosynthesis or creatine biosynthesis or for management of common disease states, such as in atherosclerosis, etc.

L-citrulline is sometimes used as a substitute for L-arginine in the management of rare genetic urea cycle enzymopathies and acquired liver disorders with hyperammonemia, and in the rare disorder, lysinuric protein intolerance. Citrulline malate (a salt of citrulline) is provided in slight amounts in a few European proprietary preparations for ill-defined or vague purposes in asthenia (weakness) or as a tonic. For liver disorders, citrulline is present with arginine and omithine in some multi-ingredient proprietory preparations. Martindale The Extra Pharmacopoeia, 30th edition, (1993).

Specifically, efficient oral management strategies for humans using L-citrulline as precursor to L-arginine have not included sickle cell disease, normal late term pregnancy, preterm labor, preeclampsia (toxemia of pregnancy), symptomatic coronary artery disease (anginal chest pain)—even with angiographically normal coronary arteries (microvascular angina), vascular patency after arterial angioplasty, focal neurologic ischemic attacks including strokes and lacunar infarctions, migraine pain, vascular/neuronal complications of hypertensive disease, endothelial injury from chronic hyperlipidemia, diabetes mellitus, aging, achalasia of the esophagus and male infertility. Francis, R. B. Jr. et al, Am. J. Hematol. 47:1405–1414, (1991); Wolters, H. J. et al, Brit. J. Haematol. 90:715–717, (1995); Steinberg, M. H., Am. J. Med. Sci. 312:167–174, (1996); Schoengold, D. W. et al, Am. J. Obstet. Gynecol. 131:490–499, (1978); Dörner, K. et al, (1993); Fitch, W. L. et al, (1987); MacDonald, P. C. et al, Scient. Am. Sci. Med. 3:42–51, (1996); Roberts, J. M. et al, Am. J. Obstet. Gynecol. 161:1200–1204, (1989); Molnar, M. et al, Am. J. Obstet. Gynecol. 170:1458–1466, (1994); Egashira, K. et al, New Engl. J. Med. 328:1659–1644, (1993); Hamon, M. et al, (1994); Morikawa, E. et al, Am. J. Physiol. 263:H1632–H1635, (1992); Caplan, L. R., Neurol. 39:1246–1250, (1989); Lauritzen, M., Sci. Med. 3:32–41, (1996); Zeiher, A. M. et al, (1993); Compo, C. et al, (1996); Ross, R. et al, Science 193:1094–1100, (1976); Bucala, R. et al, (1991); Diederich, D. et al, Am. J. Physiol. 266:H1153–H1161, (1994); Current Medical Diagnosis & Treatment, (1997); Schmidt, H. H. H. W., (1994); Schachter, A et al, J. Urol. 110:311–313, (1973); Calloway, D. H., Nutr. Absts. Revs. 53:361–382, (1983); Barbul, A., (1986).

Aging causes losses in the total number of functioning neurons. Wurtman, R. J., Sci. Am. 246:50–59, (1982). A deficiency in any key amino acid is said to limit the rate of protein synthesis and hence nutritional status. A deficiency in plasma L-arginine concentration is reported in elderly men of well-fed good health. Moriguti, J. C. et al, (1995). The free arginine concentration in cerebrospinal fluid is only about 23% of the plasma concentration of 84±22 $\mu$M (mean±SD) in fasting healthy adults. Perry, T. L. et al, (1975). Free arginine levels in many motor and sensory areas of rat brain tissue decline by 20% or more in old compared to young adult male rats. Banay-Schwartz, M. et al, J. Neurosci. Res. 26:217–223, (1990). Plasma-borne L-citrulline readily passes the blood-brain barrier. Buniatan, H. C. et al, J. Neurochem. 13:743–753, (1966).

It is unclear how arginine is transported into brain cells from the blood plasma in humans. However, L-arginine may be localized mainly within glial cells in the central nervous system, while L-citrulline and nitric oxide as co-products of neuronal c-NOS are present within nitrergic neurons. Pow, D. V., Neurosci. Lett. 181:141–144, (1994). Membrane-localized c-NOS is found in dendrites and synaptic fractions of neurons and an increase in extracellular L-arginine may result in potentiation of neuronal function. Kantor, D. B. et al, Science 274:1744–1748, (1996).

Brain tissue arginine levels follow increases in plasma levels in the rat, but they are generally only 20 to 30% of plasma levels. Buckmann, I. et al, Pharmacol. 53:133–142, (1996). L-citrulline can be converted to arginine in the brain, including perivascular nerves of cerebral arteries. Buniatan, H. C. et al, (1966); Sadasivu, B. et al, J. Neurochem 27:786–794, (1976); Chen, F. -Y. et al, J. Pharmacol. Exptl. Therap. 273:895–901, (1995).

With endothelial injury, atherosclerosis is considered to be a free radical disease. A constant source of damaging compounds is the reaction of oxygen with polyunsaturated substances in plasma and the vascular wall and the formation of oxidation products including peroxides and free radicals. Harman, D., Drugs & Aging 3:60–80, (1993). A small percentage of mitochondrial electron transport chain activity and autoxidation reactions leak electrons to reduce molecular $O_2$ to superoxide radical as the one-electron reduction product of oxygen with secondary generation of hydrogen peroxide, another reactive oxygen species. Halliwell, B., Annu. Rev. Nutr. 16:33–50, (1996). Further cell damage and atherosclerosis may result, especially with aging. Harman, D., (1993).

More free radicals are formed in experimental diabetes mellitus with endothelial cell dysfunction due to impaired vasoprotection from the L-arginine-nitric oxide pathway. Diederich, D. et al, (1994). However, nitric oxide production from endothelial nitric oxide synthase activity and endothelial-dependent vasorelaxation are masked in experimental diabetes mellitus by the increased destruction of nitric oxide by oxygen-derived free radicals like superoxide and by quenching by advanced glycolation products in diabetic endothelium and subendothelium. Bucala, R. et al, (1991); Diederich, D. et al, (1994). Thus, removal of endothelium-derived nitric oxide by metabolic-formed superoxide or by advanced glycolated products deprives smooth muscle in vascular walls of a relaxative muscle tonic effect in diabetes mellitus. In experimental diabetes mellitus, long-term oral administration of L-arginine in marked amounts prevents the glomerular hyperfiltration and abnormal filtration fraction hemodynamics and ameliorates the proteinuria. Reyes, A. A. et al, J. Am. Soc. Nephrol. 4:1039–1045, (1993).

The main function of formed nitric oxide, a free radical, as cell messenger seems to be to stimulate cell guanylate cyclase to elevate cyclic guanosine monophosphate, which in turn activates smooth muscle relaxation, platelet stability, and neurochemical potentiation. Moncada, S. et al, (1993); Schmidt, H. H. H. W. et al, (1994). Nitric oxide reacts strongly in biological systems with other metal-proteins and thiols, as well as with molecular oxygen and superoxide free radical. Stamler, J. S. et al, Cell 78:931–936, (1994).

Nitric oxide serves as a free radical scavenger by rapidly reacting with free radicals involved in lipid peroxidation and perhaps in aged-related modifications of proteins. Kanner, J. et al, Lipids 27:46–49, (1992); Stadtman, E. R., J. Gerontol. 43:B112–B120, (1988). In tissues, generated nitric oxide seems normally to be an antioxidant. Kanner, J. et al, Biochem, Biophys. 289:130–136, (1991). Mitochondria are one of the major intracellular sources of free radicals and defects in mitochondrial energy metabolism with increased production of reactive oxygen species may cause cell injury and neuronal degeneration. Nitric oxide generated by c-NOS may usually exert protective effects. Simonian, N. A. et al, Annu. Rev. Pharmacol. Toxicol. 36:83–106, (1996).

At suboptimal and depleted extracellular concentrations of L-arginine, activated nitric oxide synthase produces superoxide, highly potent peroxynitrite, and hydrogen peroxide as reactive oxygen species as mediators of cellular injury instead of nitric oxide. Xia, Y. et al, Proc. Nati. Acad. Sci. USA 93:6770–6774, (1996); Heinzel, B. et al, Biochem. J. 281:627–630, (1992).

The magnitude of intracellular L-arginine is a crucial factor in switching nitric oxide synthase from the production of nitric oxide to the production of superoxide and hydrogen peroxide. A decrease in perfusion flow may lead to tissue L-arginine depletion and cellular injury or death. Xia, Y. et al, (1996). Increasing L-arginine availability as substrate for nitric oxide synthase activity protects cells from apoptosis in an L-arginine-deficient (10 $\mu$M) environment, perhaps by alleviating oxidative stress by terminating propagation of free radical chain reactions or by interacting with oxygen and superoxide to limit their reduction to more reactive oxygen species like hydrogen peroxide and hydroxide free radical. Mannick, J. B. et al, Cell 79:1137–1139, (1994).

Inhibition of constitutive nitric oxide synthase activity during the latter part of pregnancy produces a preeclampsia-like syndrome and retardation of fetal growth in rats. Molnar, M. et al, (1994). Much evidence suggests that preeclampsia and eclampsia are human diseases, typified by vasoconstriction, that are endothelial cell disorders with endothelial injury involving the fetoplacental vessels. Roberts, J. M. et al, (1989). Basal release of nitric oxide from c-NOS activity in human umbilical arteries and veins seem important in normal pregnancies and deliveries. Chaudhuri, G. et al, Am. J. Physiol. 265:2036H–2043H, (1993).

Maternal plasma levels of most amino acids are lower in normal pregnancy than in the nonpregnant state. The plasma levels of arginine decline progressively during the first, second, and third trimesters of normal human pregnancy. In the third trimester, fasting mean "normal" values of 43.6 $\mu$M and 32 $\mu$M have been found, with 95% statistical confidence ranges from 27.8 to 71.4 $\mu$M and 8 to 68 $\mu$M, respectively. Schoengold, D. M. et al, (1978); Dörner, K. et al, (1993). After a high-protein meal, postprandial levels of plasma arginine are significantly lower than in nonpregnant women. Fitch, W. L. et al, (1987). During gestation, maternal plasma arginine levels are significantly lower in mothers of fetally malnourished infants than that in mothers having normal babies. McClain, P. E. et al, Am. J. Clin. Nutr. 31:401–407, (1978).

Addition of L-arginine to extracellular fluid bathing isolated uterine muscle strips from gravid rats results in nitric oxide generation, dose-dependent muscle relaxation, and muscle quiescence. Yallampalli, C. et al, Endocrinol. 133:1899–1902, (1993).

Oral intake of 4 to 20 grams of arginine daily may improve total sperm counts and motility rates of spermatocytes of infertile men. Schachter, A. et al, (1973). Considered as a nutritional supplement, arginine's therapeutic value in male infertility is not well documented. Calloway, D. W., (1983). However, nitric oxide generation via the l-arginine/nitric oxide pathway in testis and/or vas deferens may up-regulate spermiocytes and promote fertility. Schmidt, H. H. H. W. et al, (1994).

Achalasia is an idiopathic disorder of esophageal motility characterized by the absence of peristalsis and failure of a hypertonic lower esophageal sphincter of smooth muscle to relax during swallowing. The disorder seems to result from dysfunction or loss of nerve cells in the ganglionated myenteric plexuses and it likely involves nitrergic neurons (and perhaps submucous plexuses—W. H. W.). McQuaid, K. R. pp. 553–554 in: Current Medical Diagnosis & Treatment 1997, (1997).

In sickle cell disease, poorly understood endothelial dysfunction, intimal hyperplasias, thromboses, and vascular occlusions including strokes are characteristic. Francis, R. B. Jr. et al, (1991). Unexplained sudden death in young people is too common in sickle cell disease. Liesner, R. J. et al, J. Royal Soc. Med. 86:484–485, (1993). Sudden death following severe exercise may occur even in subjects with sickle cell trait. Kerle, K. K. et al, Mil. Med. 161:766–767, (1996). Adhesion of sickle erythrocytes to vascular endothelium is postulated to play a pivotal role in the vascular occlusions. Duits, A. J. et al, Clin. Immunol. Immunopath. 81:96–98, (1996). Low-intensity oral anticoagulation management in sickle cell disease may reverse the prothrombotic state. Wolters, H. J. et al, (1995).

Migraine is a neurologic disorder characterized by recurrent headache attacks lasting up to about 72 hours. The basic disease process seems to be a disturbed ionic homeostasis in the neuronal microenvironment following a cortical spreading wave of transient electrical depolarization. Lauritzen, M., (1996). Migraine attacks may be precipitated by different factors in various individuals via sensory afferent impulses projecting to the brain or by substances crossing the blood-brain barrier. Migraine without aura and migraine with aura are viewed identical as regards the painful pathophysiological phase of the attack, but differ at the onset of attack involving a primary disturbance of nerve cell function which may relate to mitochondrial dysfunction. Theory now is that longer-lasting microcirculatory changes follow the cortical depression with continued arteriolar vasoconstriction and arteriolar spasm focally with hypoperfusion, stasis, or ischemia. Lauritzen, M., Brain 117:199–210, (1994); Lauritzen, M., (1996).

Generation of the migraine headaches are viewed caused by secondary activation of painsensitive fibers within the walls of intracranial blood vessels (nociceptive vascular nerve fibers) including the pial arterial tree. Lauritzen, M., (1994); Lauritzen, M., (1996). Migraine pain may be triggered in some cases by nociceptive activation in dural blood vessels secondary to ischemic blood flow in the middle meningeal artery. Lambert, G. A. et al, Cephalalgia 14:430–436, (1994).

L-arginine administration reduces the oligemic vasoconstriction that follows induced cortical spreading depression in rats and raises the possibility that shortage of L-arginine contributes to reduced cerebral blood flow in migraine patients and that migraine patients might benefit from the systemic administration of L-arginine. Fabricius, M. et al, Am. J. Physiol. 269:H23–H29, (1995); Lauritzen, M., (1996). Wolff found that inhalation of small amounts of amyl nitrite, a well-known donor of nitric oxide, temporarily reversed migraine aura in some cases. Silberstein, S. D. et al, p. 115 in: Wolff's Headache and Other Head Pain, 6th ed., (1993). Also, platelet activity increases with acute migraine headaches, possibly related to physiological or other stress. DeBelleroche, J. et al, pp. 185–191 in: The Headaches, ed. J. Olesen et al, (1993).

It is known in the art that ATP (adenosine triphosphate) is the major source of chemical energy in living matter. ATP is a powerful effector of many enzymes and ATP levels are kept relatively constant in health by creatine phosphokinase and adenylate cyclase enzyme reactions. It is also known in the art that the creatine phosphokinase enzyme reaction is pivitol to good health since phosphocreatine serves as a dynamic reservoir of high-energy phosphate. This reservoir is normally high in muscle and nerve cells. Phosphocreatine buffers the high cytosolic ATP/ADP ratios from rapid fluctuations by means of the creatine phosphokinase reaction on ATP and ADP levels. Rapid fluctuations in ATP levels would be deleterious to the smooth functioning of cell cation pumps and maintaining of ionic gradients. It is also known in the art that the total creatine content in human cells is highest in muscle, brain, and testis and that free creatine serves as an energy messenger between mitochondria (the major "energy factory") and many sites of energy utilization within muscle cells, neurocytes, and many cells of the body, in the "creatine-phosphocreatine shuttle". The concentration equilibrium ratio between creatine and phosphocreatine is known to be about 0.4 to 0.5 in muscle and brain cells and there is a continuous drain or loss of phosphocreatine through a non-catalyzed cyclization to creatinine, a waste product.

Free creatine is reported high at about 14 mmol/kg in human heart muscle. Guichard, P. et al, Medical Hypotheses 45:41–44, (1995). Free creatine is high at about 8 to 9 mmol/kg in grey matter and high at about 6 mmol/kg in white matter of the human brain. Michaelis, T. et al, Radiology 187:219–227, (1993). Besides serving as reactant for phosphocreatine formation, creatine may serve a cytoprotective role as an amine to scavenge intracellular hexose or triose sugars formed at undue levels in diabetes mellitus (or aging—W. H. W.). Guichard, P. et al, (1995). Deleterious non-enzymatic reactions between glucose or phosphorylated sugar intermediates and amine groups of protein side-chains might take place leading to adversely modified protein products (Maillard products) or advanced glycolated products. Guichard, P. et al, (1995). Advanced glycolated products are capable of quenching nitric oxide formed by constitutive nitric oxide synthases. Bucala, R. et al, (1991).

Extracellular creatine increased by 3 mM in hippocampal brain tissue in vitro results in large increases in neuronal free creatine and phosphocreatine levels without change in ATP levels. Degrees of anoxia-induced neuronal damage are attenuated and greater neurocyte viabilities result after anoxic periods. Carter, A. J. et al, J. Neurochem. 64:2691–2699, (1995).

Oral supplementation of creatine daily in healthy normal humans leads to lessened muscle fatigue with physical exercise. The creatine supplementation is associated with greater muscle stores of free creatine and phosphocreatine. Harris, R. C. et al, Clinical Sci. 83:367–374, (1992). Fatiguing myocytes produce reactive oxygen species at a dramatically increased rate and seem to be responsible for at least some of the fatigue. Concurrently, constitutive nitric oxide synthases in the mitochondrial membranes of the myocytes produce more nitric oxide. Reid, M. B., News Physiol. Sci. 11:114–119, (1996).

It is known in the art that spermatozoa contain large concentrations of creatine. It is also known that the concentration of arginine in seminal ejaculates averages normally about 4.5 mM in subjects with normospermia. Addition of L-arginine in vitro to human semen specimens with low motility enhances sperm motility in a concentration-dependent manner between 1.0 and 4.0 mM. Keller, D. W. et al, Biol. Reproduct. 13:154–157 (1975).

It is known in the art that L-arginine is an essential precursor for the biosynthesis of creatine in the human body in a 2-step enzymatic process. Glycine amidinotransferases are present in kidney, liver, and other tissues for the transfer of the guanidino group of L-arginine to glycine to yield guanidoacetate, the immediate precursor of cell creatine.

Low-dose acetylsalicylic acid (aspirin) intake in humans inhibits platelet activity and prolongs the total bleeding time. These effects are associated with beneficial therapeutic effects in subjects with cardiovascular disease. Boysen, G. et al, Stroke 15:241–243, (1984).

DETAILED DESCRIPTION OF INVENTION

This invention relates to the peroral administration of L-citrulline to humans in daily amounts greater than that ingested usually by dietary means as constituents of food proteins and in food juices. This invention is an example of orthomolecular medicine, a term conceived and put into public domain by L. Pauling in a 1967 presentation by proxy. Pauling, L., (1968). This invention uses the method of oral supplementation by sizable amounts of L-citrulline, a substance normally present in humans, as precursor substance to increase and to sustain efficiently augmented blood plasma concentrations of L-arginine by bioconversions as potentially available reactant or substrate for cell purposes in the preservation of better health and for the treatment of numerous disease conditions.

L-citrulline is a naturally occurring amino acid present in melon juices and as a protein constituent in food plants of the Cucurbitaceae family, such as melons, cucumbers, squash, and pumpkin. L-citrulline may be obtained by protein hydrolysis, by synthesis, or by fermentation. Industrial production with high yields is currently done by fermentation to those skilled in the art. L-citrulline is commercially available in highly purified form (99+%) by select distributors of fine chemicals, for example ICN Pharmaceuticals, Inc., Costa Mesa, Calif., USA; Acros Organics, N.J., USA and Geel, Belgium; and Sigma Chemical Co., St. Louis, Mo., USA.

I have contemplated and discovered that human blood plasma concentrations of free L-arginine are promptly raised to much higher levels after single oral doses of 3.0 grams or more of L-citrulline in capsule form. Also, I have discovered that daily dosage in two divided subdoses results efficiently in greater blood plasma levels of L-arginine even after overnight fasting for 9 to 10 hours. The method is a more efficient and longer lasting method to elevate blood plasma L-arginine levels in man than by ingestion of equivalent amounts of L-arginine as single amino acid or present in protein meals. Yearick, E. S. et al, (1967); Palmer, T. et al, (1973); Smoyer, W. E., (1991).

I contemplate that ingested L-citrulline is absorbed efficiently and like intestinally derived citrulline made from circulating glutamine that the amino acid passes in portal venous blood through the human liver without appreciable organ uptake, as it does in the rat. Windmueller, H. G. et al, (1981). The L-citrulline is contemplated to be distributed then to the kidneys, glial cells, and neurocytes of the brain, endothelial cells, muscle cells, and other cells, for de novo synthesis of L-arginine locally or for redistributions as L-arginine systemically to other cells.

Embodiments include more available L-arginine for cytoplasmic and nuclear protein biosynthesis, for more available rate-limiting substrate to activated constitutive nitric oxide synthases for more production of nitric oxide as second messenger for vasoprotection, circulating platelet stability, relaxative smooth muscle tone, etc. and for more nitric oxide protection as scavenger of other, deleterious reactive oxygen species arising from metabolic oxidative stress. Another embodiment is more circulating L-arginine that is available to increase the stores of free creatine and phosphocreatine in muscles (skeletal, cardiac, and smooth), the brain, and other tissues.

The creatine-synthesing enzyme system from L-arginine and glycine is known to be widely distributed in human tissues including brain, muscle, kidneys, and liver. It is also known that dietary arginine in man leads to more creatine biosynthesis and slowly expansible pools of creatine and phosphocreatine in muscle and nerve tissues. Walker, J. B., Adv. Enzymol. 50:178–242, (1979). I devise that increased muscle and neural stores of free creatine, resulting from oral L-citrulline supplementation, may serve as more concentrated creatine scavenger as free amine to decrease the potential increase of undue amounts of hexose and triose intermediates that may adduct adversely to form glycolated protein products in diabetes mellitus and aging. It is also devised that muscle and brain stores of phosphocreatine, increased by concentration-dependency means by induced greater levels of L-arginine and creatine, serve as greater ergogenic reservoirs to many pivotal chemical processes. Muscle and neural fatigue with continuting metabolic activity and oxidative stress will thereby be ameliorated or delayed.

I contemplate that the activated constitutive nitric oxide synthases for physiologic or homeostatic purposes are rate-limited by L-arginine because of the simultaneous concentrations of L-glutamine or other inhibitory substances in the "arginine paradox" phenomenon that is devised to take place in living man. It is contemplated that the activities of activated constitutive nitric oxide synthases from L-arginine and the activities of glycine amidinotranferases from L-arginine for cell creatine synthesis in muscle and neural cells are effectively both apparent firstorder enzymatic reactions. In these reactions, the velocity of the catalyzed reaction is devised roughly to be proportional to the concentration of the initial reactant, L-arginine, even at greater than 90 or 100 $\mu$M normal plasma levels of L-arginine.

I devise, after L. Pauling, (1968), that there exist considerable human individualities in the concentrations and abilities of the many constitutive nitric oxide synthases and of the cell amidinotranferases of L-arginine to glycine for making creatine. I contemplate that increased oral supplementation with L-citrulline leads to increased blood plasma, interstitial fluid, and cell levels of L-arginine to more fully saturate these enzymes both in normal, healthy persons and in individuals with reduced catalytic activities of these enzymes in disease states. Increased reactant levels induced uniquely by L-citrulline supplemention is devised to cause the enzyme reactions to take place at more normal or superior velocities. It is contemplated that better preservation of good health and better treatment of many altered states will result with application of this method of orthomolecular medicine.

Specific embodiments of the invention are for prophylaxis and management of the following conditions: good health; sickle cell disease; sickle cell trait; migraine and migraine syndrome; transient ischemic attack, ischemic stroke, and lacunar infarction; coronary artery and peripheral atherosclerotic disease; coronary artery and peripheral angiospastic disease; restenosis after angioplasty; normal pregnancy; preclampsia; spontaneous preterm labor; male infertility; diabetes mellitus; aging; continuing increased muscle and brain activities, and achalasia.

The invention is illustrated by the following examples.

EXAMPLE 1

A novel calorimetric method for the quantitative assay of free L-arginine in blood plasma was developed. The method measures the color product from monosubstituted guanidines without and with L-arginase incubation to destroy the arginine and the potential guanido color product that would be derived from L-arginine. The photometric decrease in guanido color product measures specifically the concentration of L-arginine. The L-arginine methodology was applied to ultrafiltrates of blood plasma after ultrafiltrations of separated plasma samples were done at 4° Celsius.

Figure 1:
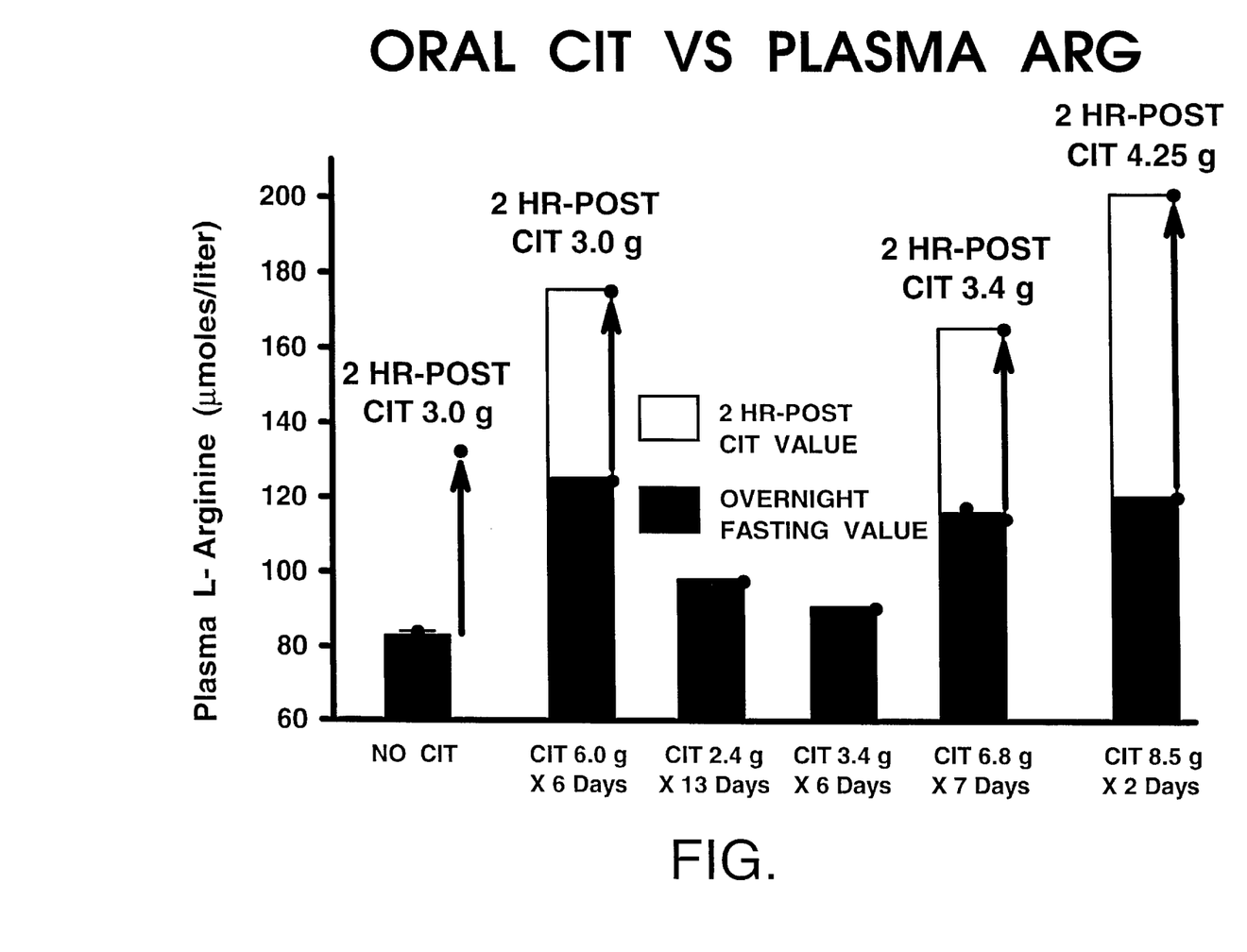

A 71-year old male American of Northwest European ancestry was studied over several weeks. His body weight was 102 kg. He remained on his usual regular diet and continued working during the study. The results in the study are shown in graph form in the FIGURE.

Blood plasma levels after 9 to 10 hours of overnight fasting averaged $83.0\pm1.1$ $\mu M$ (mean±SD of 3 determinations). Two hours after ingestion of 3.0 grams of L-citrulline in capsular form, plasma L-arginine level rose by 62.4% to 132.7 $\mu M$. Overnight fasting plasma levels of L-arginine measured 125.2, 98.1, 90.8, 114.2, and 120.0 $\mu M$ after ingestion of L-citrulline for 6 days at 6.0 grams, for 13 days at 2.4 grams, for 6 days at 3.4 grams, for 7 days at 6.8 grams, and for 2 days at 8.5 grams, respectively, in 2 divided doses (morning and nightly).

After an overnight fasting period, ingestion of additional L-citrulline in single dosage of 4.25 grams resulted in increment of plasma L-arginine level to 200.6 $\mu M$ (see the FIGURE.) No adverse symptoms or untoward signs were experienced during the study.

EXAMPLE 2

The same subject that was studied in Example 1 was studied by total bleeding time determinations before and during ingestion of daily doses of L-citrulline, in two divided subdoses. Forearm bleeding times were done by 3 to 5 mm cuts about 1 mm deep made perpendicular to the fold of the elbow during template methodology and a sphygmomanometer cuff maintained near 40 mm Hg pressure. Control bleeding times were 5½ minutes. Bleeding time rose to 13½ minutes after 2 days of ingestion of 8.5 grams daily. Bleeding time was prolonged at 13 minutes after 4 weeks of ingestion of 5.4 grams of L-citrulline daily in 2 divided doses.

Thus, oral supplementation with L-citrulline in daily doses of 5.4 grams to 8.5 grams prolongs total bleeding time about two-fold. After small therapeutic doses of aspirin orally, total bleeding times are also prolonged. Boysen, G., (1984).

EXAMPLE 3

The method described in EXAMPLE 1 was used also in subjects with sickle cell anemia. Plasma was obtained from venous blood specimens of 12 subjects with sickle cell anemia not in acute vasoocclusive crises. Subject blood was obtained about 2 to 3 hours after a light breakfast or noon meal.

Plasma ultrafiltrate L-arginine concentrations averaged $56.6\pm15.3$ micromolar (mean±1 standard deviation) in the 12 subjects. The range in plasma L-arginine levels was from 26.4 to 74.4 $\mu M$ in the 12 subjects. Their ages ranged from 4½ to 24 years of age. The subjects were African Americans, half were males and half were females.

Thus, all of the subjects were found to have plasma arginine values lower than average normal value. The mean value was very much lower than the expected normal value. Two-hour postprandial or nonfasting arginine levels in plasma measured by the method of HPLC in normal children generally average near 115 $\mu M$. The results suggest that deficiency of L-arginine may be a key factor leading to symptomatology in sickle cell anemia. Endothelial and subendothelial hyperplasias and vascular occlusions are major complications in sickle cell anemia.

EXAMPLE 4

Oral supplementation with L-citrulline capsules was done by a woman 44-years old and of Northwest European ancestry. Her body weight was 59 kg. The subject gave a history of migraine pains with and without aura for about 15 years. Currently, the migraine pains were recurring about once to a few times weekly. Her mother had experienced migraine headaches for many years.

Shortly after the onset of a severe headache attack, the subject ingested 2.7 grams of L-citrulline, followed by another 2.7 grams about 1 hour later. She ingested a third dose of the same amount 6 hours later. The pain markedly lessened in intensity and in duration. Much less nausea was experienced during the migraine attack.

Many variations will be obvious to those skilled in the art. Thus, the invention is defined by the claims:

What is claimed is:

1. A method of improving the health of a subject to increase the plasma concentration of arginine in the subject to a level from a low or normal fasting concentration to a level which is up to three times an average overnight fasting arginine level of about 90 $\mu$mole per liter of plasma, comprising orally administering L-citrulline as precursor substance.

2. The method according to claim 1, wherein the subject is in normal or good health.

3. The method according to claim 1, wherein the subject has sickle cell disease.

4. The method according to claim 1, wherein the subject has sickle cell trait.

5. The method according to claim 1, wherein the subject has migraine or migraine syndrome.

6. The method according to claim 1, wherein the subject has transient ischemic attack, ischemic stroke, or lacunar infarction of the brain.

7. The method according to claim 1, wherein the subject has coronary artery atherosclerotic disease or coronary vasospastic disease.

8. The method according to claim 1, wherein the subject has peripheral atherosclerotic disease or peripheral angiospastic disease.

9. The method according to claim 1, wherein the subject has restenosis after angioplasty.

10. The method according to claim 1, wherein the subject is in the latter two-thirds of normal pregnancy.

11. The method according to claim 1, wherein the subject has toxemia of pregnancy.

12. The method according to claim 1, wherein the subject has spontaneous preterm labor.

13. The method according to claim 1, wherein the subject has made infertility with oligospermia or impaired sperm motility.

14. The method according to claim 1, wherein the subject has diabetes mellitus or aging.

15. The condition according to claim 1, wherein the subject is in a condition of increased or continuing brain or neural activities.

16. The condition according to claim 1, wherein the subject has much increased or continuing muscular activities.

17. The condition according to claim 1, wherein the subject has achalasia.

18. The method of claim 1, wherein the oral L-citrulline is used in humans in acute dosage range from about 2.5 to 25 grams per day, in 2 or more divided doses, or in chronic dosage range from about 1.8 grams to about 15 grams per day, in 2 or more divided doses.

19. The method of claim 1, wherein the supplementation with L-citrulline is in capsule, tablet, or liquid form either as sole active ingredient or with L-ascorbic acid as a second active co-ingredient.

* * * * *

(12) EX PARTE REEXAMINATION CERTIFICATE (10443rd)
United States Patent
Waugh (10) Number: US 6,028,107 C1
(45) Certificate Issued: *Dec. 19, 2014

(54) ORTHOMOLECULAR MEDICAL USE OF L-CITRULLINE FOR VASOPROTECTION, RELAXATIVE SMOOTH MUSCLE TONE AND CELL PROTECTION

(75) Inventor: William Howard Waugh, Greenville, NC (US)

(73) Assignee: Tawnsaura Group LLC, Newport Beach, CA (US)

Reexamination Request:
No. 90/012,962, Aug. 29, 2013

Reexamination Certificate for:
Patent No.: 6,028,107
Issued: Feb. 22, 2000
Appl. No.: 08/807,757
Filed: Feb. 27, 1997

( * ) Notice: This patent is subject to a terminal disclaimer.

(51) Int. Cl.
*A61K 31/195* (2006.01)
*A61K 31/198* (2006.01)
*A61K 33/12* (2006.01)
*A61K 33/06* (2006.01)

(52) U.S. Cl.
CPC ............... *A61K 31/198* (2013.01); *A61K 33/12* (2013.01); *A61K 33/06* (2013.01); *A61K 2300/00* (2013.01)
USPC .......................................... 514/563; 514/561

(58) Field of Classification Search
None
See application file for complete search history.

(56) References Cited

To view the complete listing of prior art documents cited during the proceeding for Reexamination Control Number 90/012,962, please refer to the USPTO's public Patent Application Information Retrieval (PAIR) system under the Display References tab.

*Primary Examiner* — Evelyn Huang (57) ABSTRACT

This invention is a novel method in orthomolecular medicine to sustain favorable amounts of L-arginine efficiently within the human body for preservation of good health and amelioration of various disease states. The method provides administration of sizable amounts of L-citrulline as precursor substance for bioconversion to L-arginine in order to maintain greater blood plasma concentrations of L-arginine as potential substrate for various metabolic functions. The method is useful to increase the availability of substrate for nitric oxide production by constitutive nitric oxide synthases. Embodiments include uses of exogenous L-citrulline for more vasoprotection in sickle cell disease and atherosclerosis, more stability in circulating platelets, more relaxative smooth muscle tone during pregnancy and in achalasia, greater defense against restenosis after angioplasty, greater defense against oxidative stress, enhanced cell stores of creatine, and enhanced fertility in males with oligospermia.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 2, 15, 16, 18 and 19 are cancelled.

Claims 3-14 and 17 were not reexamined.

\* \* \* \* \*